US010156531B2

(12) United States Patent
Kwak et al.

(10) Patent No.: US 10,156,531 B2
(45) Date of Patent: *Dec. 18, 2018

(54) MEASURING CONNECTIVITY BETWEEN DIFFERENT PORE TYPES IN POROUS MEDIA (71) Applicant: Saudi Arabian Oil Company, Dhahran (SA)

(72) Inventors: Hyung T. Kwak, Dhahran (SA); Ali Abdullah Al-Yousef, Dhahran (SA); Salah Hamad Al-Saleh, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 158 days.

This patent is subject to a terminal disclaimer.

(21) Appl. No.: 15/333,938

(22) Filed: Oct. 25, 2016

(65) Prior Publication Data
US 2017/0115242 A1  Apr. 27, 2017

Related U.S. Application Data (60) Provisional application No. 62/246,710, filed on Oct. 27, 2015.

(51) Int. Cl.
G01R 33/44 (2006.01)
G01N 15/08 (2006.01)
(Continued)

(52) U.S. Cl.
CPC ........ *G01N 24/081* (2013.01); *G01N 15/08* (2013.01); *G01R 33/448* (2013.01); *G01R 33/46* (2013.01)

(58) Field of Classification Search
CPC . G01V 3/32; G01V 3/14; G01V 11/00; G01V 1/50; G01V 3/18; G01V 3/38;
(Continued)

(56) References Cited

U.S. PATENT DOCUMENTS 5,838,155 A   11/1998  Bowers
6,069,477 A    5/2000  Chen et al.
(Continued)

OTHER PUBLICATIONS

Fleury et al., "Quantitative analysis of diffusional pore coupling from T2—store—T2 NMR experiments", Journal of Colloid and Interface Science, Apr. 5, 2009, pp. 250-259, vol. 336, Elsevier.
(Continued)

*Primary Examiner* — Ruifeng Pu
(74) *Attorney, Agent, or Firm* — Bracewell LLP; Contance G. Rhebergen; Albert B. Kimball, Jr.

(57) ABSTRACT

The connectivity between different pore types in porous media is measured by using low-field nuclear magnetic (NMR) and fast field cycling NMR techniques. Due to the fluid exchange between connected pores, $T_1(T_2)$ NMR relaxation times of proton nuclei of fluids in the different pore types are shifted. By comparing the $T_1(T_2)$ NMR relaxation times of porous media samples which are 100% brine saturated with relaxation times for the samples containing brine and hydrocarbon in the different pore systems of the samples, the connectivity between the pores can be measured.

9 Claims, 6 Drawing Sheets (51) Int. Cl.
*G01N 24/08* (2006.01)
*G01R 33/46* (2006.01)

(58) Field of Classification Search
CPC .. G01N 24/081; G01N 24/084; G01N 15/082; G01N 3/32; G01R 33/383; G01R 33/448; G01R 33/56341; G01R 33/3806; G01R 33/3808; G01R 33/445; G01R 33/4835; G01R 33/50; G01R 33/54; Y02A 90/344
See application file for complete search history.

(56) References Cited

U.S. PATENT DOCUMENTS

| | | | |
|---|---|---|---|
| 7,295,927 B2* | 11/2007 | Clavaud | G01V 1/50 702/7 |
| 2003/0034777 A1* | 2/2003 | Chen | G01V 3/32 324/303 |
| 2003/0107374 A1* | 6/2003 | Chen | G01N 24/081 324/303 |
| 2003/0231017 A1* | 12/2003 | Kiesl | E21B 33/1243 324/303 |
| 2008/0221800 A1* | 9/2008 | Gladkikh | G01V 3/32 702/11 |
| 2009/0189604 A1* | 7/2009 | Romero | G01N 24/081 324/303 |
| 2009/0248311 A1* | 10/2009 | Coope | G01N 24/084 702/13 |
| 2010/0109664 A1* | 5/2010 | Minh | G01V 3/32 324/303 |
| 2014/0035574 A1* | 2/2014 | Sun | G01V 3/14 324/303 |
| 2014/0107928 A1* | 4/2014 | Roy | G01V 3/32 702/7 |
| 2014/0285196 A1* | 9/2014 | Liu | G01N 24/081 324/309 |
| 2015/0219782 A1* | 8/2015 | Kadayam Viswanathan | G01V 3/32 324/309 |
| 2018/0259468 A1* | 9/2018 | Kwak | G01R 33/46 |

OTHER PUBLICATIONS

Arns et al., "Pore Scale Characterization of Carbonates Using X-ray Microtomography", SPE Annual Technical conference and Exhibition Houston Texas, 2004, pp. 1-10, SPE90368.

Boever et al., "Quantification and Prediction of the 3D Pore Network Evolution in Carbonate Reservoir Rocks", Oil & Gas Science and Technology, 2012, pp. 161-178, vol. 67, No. 1, IFP Energies nouvelles.

Dong et al., "Pore Network Modeling: Analysis of Pore Size Distribution of Arabian Core Samples", 15th SPE Middle East Oil & Gas Show and Conference held in Bahrain International Exhibition Centre, 2007, pp. 1-5, SPE 105156.

Fleury, "Characterization of Pore to Pore Diffusive Exchange Using NMR T2-Store-T2 2D Experiments", International Symposium of the Society of Core Analysts held in Noordwijk, the Netherlands, 2009, pp. 1-12, SCA2009-21.

Jul 30, 2015Chemmi, et al: "A Comprehensive Multiscale Moisture Transport Analysis: From Porous Reference Silicates to Cement-Based Materials," European Physical Journal, Special Topics, vol. 224, No. 9, Jul. 30, 2015, pp. 1749-1768.

Korb et al., "Dynamical surface affinity of diphasic liquids as a probe of wettability of multimodal porous media", Physical Review, 2009, pp. 1-12, vol. 80, The American Physical Society.

Korb, "Nuclear Magnetic Relaxation of Liquids in Prous Media;" New Journal of Physics, Institute of Physics Publishing, vol. 13, No. 3, Mar. 22, 2011, p. 35016; 26 pp.

Monteilhet et al., "Observation of exchange of micropore water in cement pastes by two-dimensional T2-T2 nuclear magnetic resonance relaxometry", Physical Review E, 2006, pp. 1-9, The American Physical Society.

Neethirajan et al., "Network Analysis of Grain Bulk Pore Structure Using High Resolution X-ray Computed Tomography Images", CSBE—SCGAB Annual General Meeting Sponsored by CSBE Edmonton Alberta, 2006, pp. 1-17, The Canadian Society for Bioengeering.

Lowden, B.D., et al: "T2 Relaxation Time Versus Mercury Injection Capillary Pressure: Implications for NMR Logging and Reservoir Characterisation.", SPE 50607, SPE European Petroleum Conference, Oct. 20, 1998, pp. 323-327.

Borgia, G. C.; "A New Untree Fluid Index in Sandstones Through NMR Studies," SPE 28366; SPE Formation Evaluation, SPE Annual Technical Conference and Exhibition, vol. 11, No. 2, Sep. 25, 1994, pp. 89-93.

Sok et al., "Pore Scale Characterization of Carbonates at Multiple Scales: Integration of Micro-CT, BSEM and FIBSEM", International Symposium of the Society of Core Analysts held in Noordwijk, The Netherlands, 2009, pp. 1-12, SCA 2009-18.

* cited by examiner

MEASURING CONNECTIVITY BETWEEN DIFFERENT PORE TYPES IN POROUS MEDIA

CROSS-REFERENCE TO RELATED APPLICATIONS

This application claims priority from U.S. Provisional Application No. 62/246,710, filed Oct. 27, 2015. For purposes of United States patent practice, this application incorporates the contents of the Provisional application by reference in entirety.

BACKGROUND OF THE INVENTION

1. Field of the Invention

The present invention relates to measuring connectivity between different pore types in porous media of subsurface formations, and more particularly to measuring connectivity with low-field nuclear magnetic resonance and fast field cycling nuclear magnetic resonance measurements.

2. Description of the Related Art

Nuclear magnetic resonance (or NMR) measurements whether in well logging of in situ formations or in laboratory testing of formation rock samples is used as a reliable porosity measurement technique since NMR measurements are not dependent on lithology. Thus, NMR data is often used for reserve estimation by identifying the movable and immovable fluids in the reservoir rocks. Accurate reserve estimation from NMR logging and laboratory data, however, is quite challenging due to the presence of diffusion coupling for complicated pore systems in carbonate rocks.

Currently, so far as is known, pore connectivity cannot be measured accurately from NMR logging data. Therefore, what is known as a NMR $T_2$ cutoff value for NMR logging data is obtained from the NMR data, based on the laboratory measurement from a selected rock sample from the reservoir of interest. This method is an approximation and has been subject to a large margin of error due to its being based on statistical estimates. Other pore connectivity laboratory measurements are based on sonic and electric current resistivity within porous media, which is a different measure from fluid connectivity, since sonic and electric current resistivity do not take into account capillary pressure. Fluid connectivity is based on capillary pressure within the rock sample being a main factor which controls the fluid flow in the porous media.

Pore connectivity determination by X-ray microcomputed tomography (or microCT) techniques has been used. However, there are disadvantages. The X-ray microCT technique determines the rock structural connectivity based on an X-ray microcomputed tomographic image, which is different from pore connectivity of fluids in the porous media of the rock. It requires the cut-off value to determine the pores and solid matrix. X-ray microCT imaging requires a very small rock sample size to achieve a high resolution (~4 μm/voxel) image. This size sample is the minimum resolution requirement to observe micro-pores of most carbonate rocks. This sample size is too small to be a representative volume of carbonate rocks which have relatively heterogeneous pore distribution. The most common sample size for a rock sample is a 1 mm³ cube, which is considerably larger than that required for X-ray microCT imaging.

Prior art techniques have been able to distinguish between fluid types (hydrocarbon and water) in rock samples pores by identifying biphasic behavior of water and hydrocarbon, but so far as is known not to determine connectivity between different pore types.

SUMMARY OF THE INVENTION

Briefly, the present invention provides a new and improved method of obtaining a measure of connectivity between pores in a rock sample from a subsurface hydrocarbon reservoir. Nuclear magnetic resonance relaxation times are obtained of the rock sample fully saturated with water. A nuclear magnetic resonance dispersion profile of the rock sample is obtained at irreducible water saturation, and nuclear magnetic resonance relaxation times of the rock sample are also obtained at irreducible water saturation. Nuclear magnetic resonance relaxation times are then obtained of the rock sample fully saturated with a hydrocarbon liquid. A measure of connectivity between pores of pores in the rock sample is then obtained based on the obtained measures of nuclear magnetic resonance relaxation times of the rock sample: when fully saturated with water; when at irreducible water saturation; when fully saturated with a hydrocarbon liquid; and the nuclear magnetic resonance dispersion profile.

The present invention also provides a new and improved method of obtaining a measure of connectivity between pores in a rock sample. Nuclear magnetic resonance relaxation times are obtained of the rock sample fully saturated with water. A nuclear magnetic resonance dispersion profile of the rock sample is obtained at irreducible water saturation, and nuclear magnetic resonance relaxation times of the rock sample are also obtained at irreducible water saturation. Nuclear magnetic resonance relaxation times are then obtained of the rock sample fully saturated with a hydrocarbon liquid. A measure of connectivity between pores of pores in the rock sample is then obtained based on the obtained measures of nuclear magnetic resonance relaxation times of the rock sample: when fully saturated with water; when at irreducible water saturation; when fully saturated with a hydrocarbon liquid; and the nuclear magnetic resonance dispersion profile.

DETAILED DESCRIPTION OF THE PREFERRED EMBODIMENTS

Figure 1A:
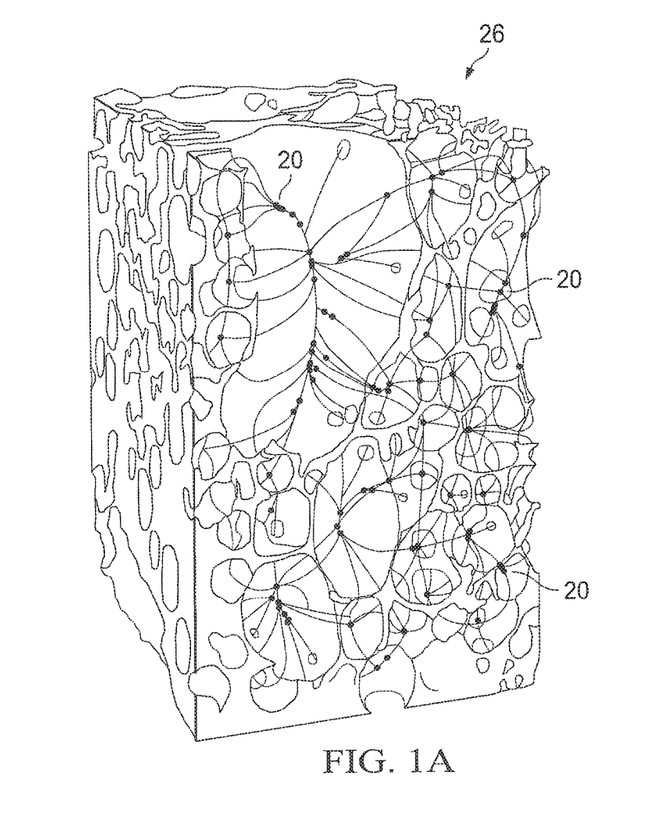
FIGS. 1A, 1B, and 1C are displays of three-dimensional pore network models formed by prior art micro x-ray techniques.
Figure 1B:
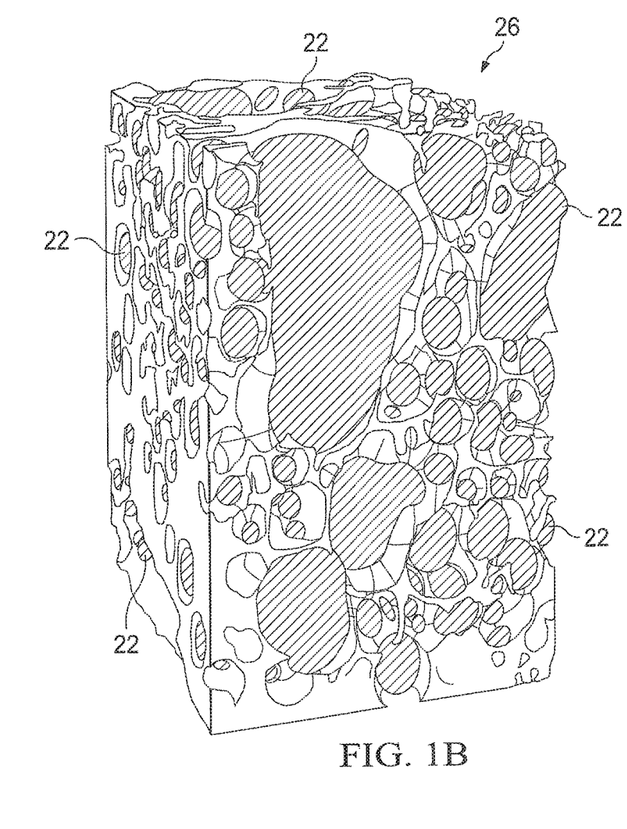
Figure 1C:
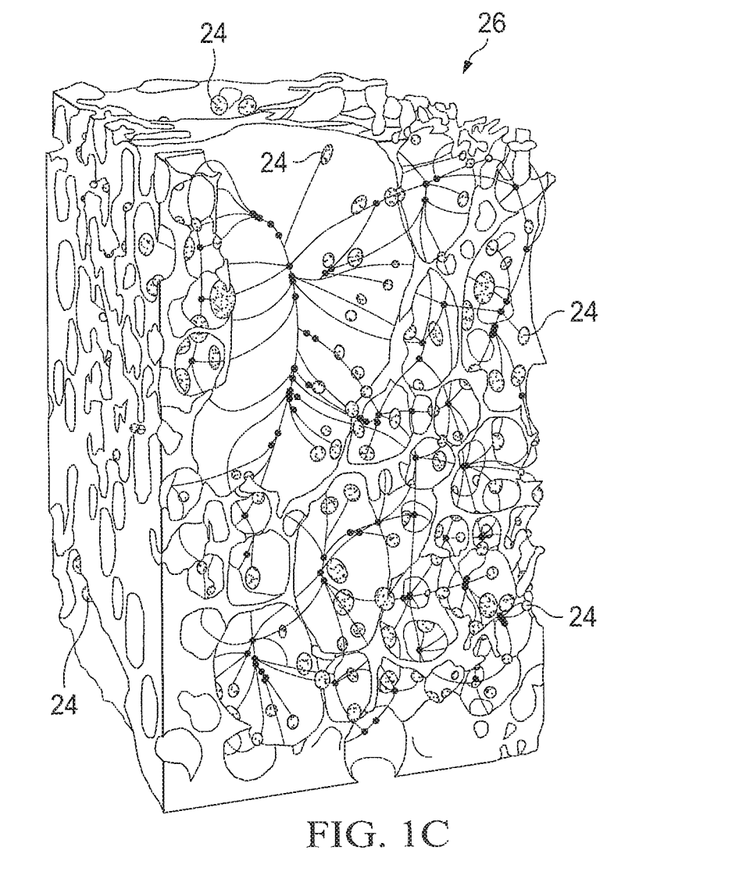

In the drawings, FIGS. 1A, 1B, and 1C are displays of three-dimensional network models formed by prior art micro x-ray CT techniques. The models show at 20, 22, and 24, respectively, different fluid diffusion coupling within an example given pore structure 26 for the presence of different types of fluids. FIGS. 1A, 1B, and 1C thus illustrate an example rock sample 26 having pore distributions with different pore connectivity due to diffusion coupling. However, as mentioned, so far as is known micro x-ray CT methods require rock samples which are too small to be representative of a carbonate rock which has a relatively heterogeneous pore distribution. Thus, a rock sample for micro x-ray CT pore connectivity determination might not accurately represent formation carbonate rock of interest.

Figure 2A:
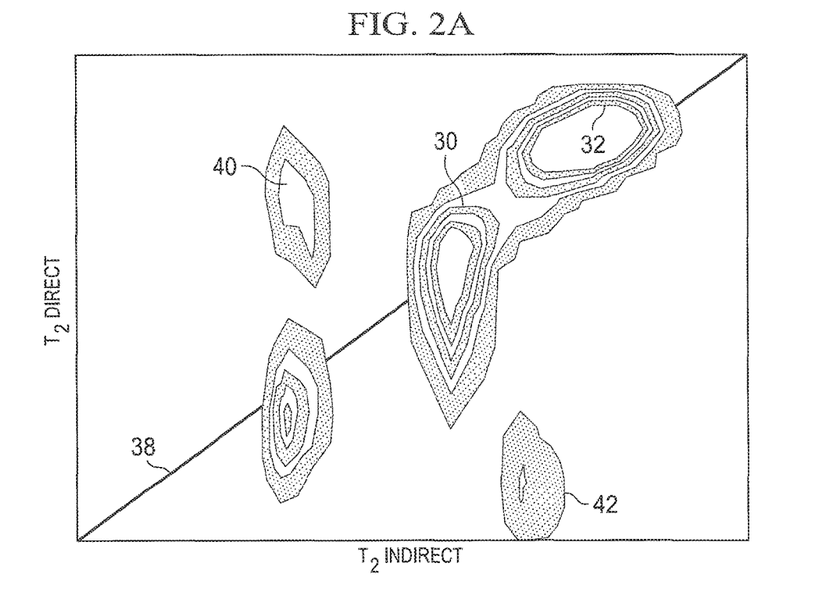
FIGS. 2A and 2B are example two-dimensional $T_2$-$T_2$ maps of prior art NMR measurements.
Figure 2B:
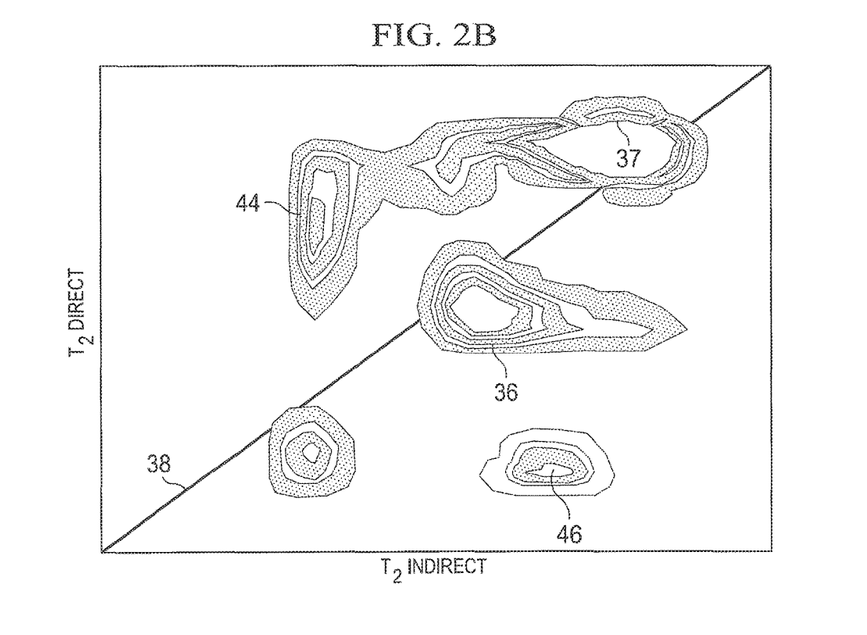

FIGS. 2A and 2B are example logarithmic exchange plots of NMR measurements at different relaxation or $T_2$ times. FIGS. 2A and 2B are example two-dimensional $T_2$-$T_2$ maps of prior art NMR $T_2$-$T_2$ exchange measurements at two different store times. In this example, the fluid is brine. As can be seen, the maps are plotted as logarithmic time functions with $T_2$ direct as a function of $T_2$ indirect. As shown, peaks such as 30 and 32 of FIG. 2A as compared to peaks 34 and 36 of FIG. 2B in what is known as diagonal 38 are indicative of the different pore systems. Similarly, peaks such as 40 and 42 in FIG. 2A, and 44 and 46 in FIG. 2B, respectively, show fluid connectivity between pore systems. As can be seen, and as previously mentioned, the presence of diffusion coupling in complicated pore systems of carbonate rock as has made accurate measurement of pore connectivity a challenging approximation.

According to the present invention, accurate measures of the fluid connectivity of the pores within carbonate rocks are obtained from the NMR logging and laboratory data in order to form estimates of reservoir reserves. With the present invention, it has been found that due to the fluid exchange between connected pores in a rock sample, the $T_1(T_2)$ NMR relaxation times of proton nuclei of fluids in the different pore types obtained as NMR measures are time shifted.

Longer relaxation times gets shorter and shorter relaxation time gets longer due to such fluid exchange. It has been found that the NMR relaxation time shift depends on the strength of diffusion coupling between different pore types. The amount of the NMR relaxation time shift can vary significantly based on such diffusion coupling. The strength of diffusion coupling can thus be translated to the connectivity. By comparing the $T_1(T_2)$ NMR relaxation time of a porous media sample which is 100% brine saturated with the $T_1(T_2)$ NMR relaxation time for the same sample when saturated with brine and hydrocarbon in different pore systems of that sample, the connectivity between these pores can be measured. As will be set forth, a nuclear magnetic resonance dispersion (NMRD) profile is also obtained according to the present invention. The NMRD profile is obtained by fast field cycling nuclear magnetic resonance (FFC-NMR) techniques and is used to identify the fluid segregation between different pore types.

Figure 3:
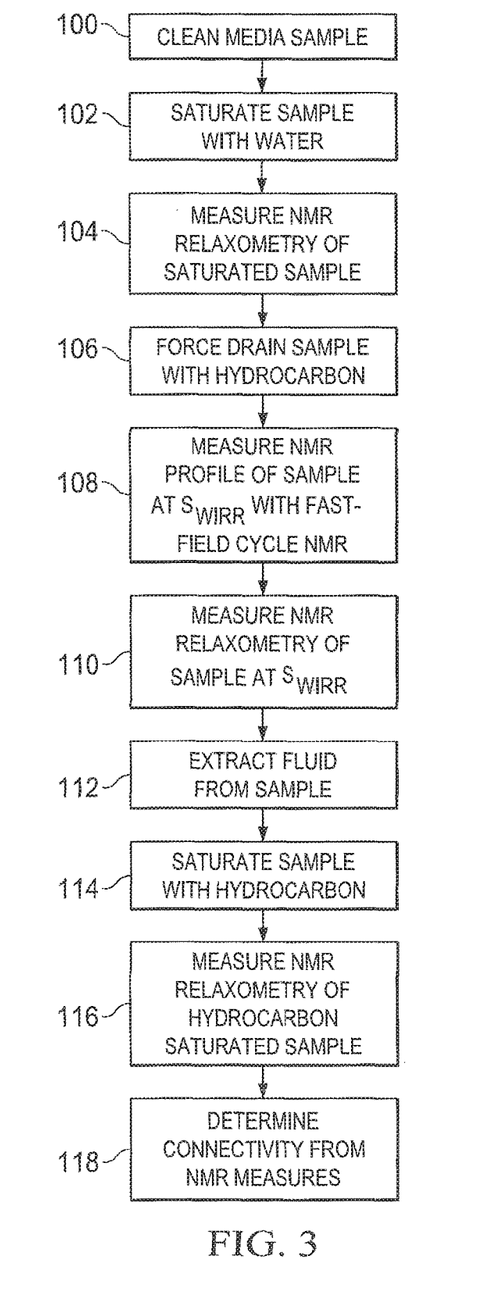
FIG. 3 is a schematic diagram of a process for measuring connectivity between different pore types in porous media according to the present invention.

The pore connectivity for fluids transfer between pores in a rock sample can be measured by:

$$\text{Connectivity} = \left(1 - \frac{A}{B}\right) \quad (1)$$

where $A = T_{1LM}$ (or $T_{2LM}$), in which the subscript LM stands for logarithmic mean, between two pores saturated with brine; and $B = T_{1LM}$ (or $T_{2LM}$) between two pores when the pores are saturated with hydrocarbon at $S_{wirr}$, or irreducible water saturation. In the hydrocarbon saturated rock sample, only small pores are only saturated with brine due to irreducible water saturation, while the large pores of the sample are saturated with hydrocarbon. The segregation of different fluids in different pore systems is achieved according to the present invention, as will be described below. A comprehensive methodology of measuring connectivity between different pore types in porous media according to the present invention is illustrated schematically in FIG. 3.

As indicated at step 100, the porous media sample is first cleaned in the conventional manner, with a series of organic solvents to achieve water-wet porous media. During step 102, the rock sample is fully saturated, either with brine or de-ionized water.

During step 104, measures of $T_1(T_2)$ NMR relaxometry are taken with a suitable low-field NMR instrument with an external magnetic field usually lower than 1 Tesla to obtain $T_1(T_2)$ distributions of pores in the sample (parameter A of Equation (1) above).

During step 106, forced drainage of the sample with hydrocarbon is performed, preferably pure alkane liquids although other solvents could be used, until irreducible water saturation or $S_{wirr}$ is reached in the rock sample. With the rock sample at irreducible water saturation, it is desirable to confirm fluid isolation in the multiple pore system of the sample.

Step 108 involves measuring an NMRD profile of the sample at $S_{wirr}$ by FFC NMR techniques with a Fast Field Cycling NMR instrument. The variation of external magnetic field strength for the NMRD profile preferably ranges from 10 k Hz up to tens of MHz which is enough to show the different characteristics of brine and hydrocarbon on the pore surface. The NMRD profile obtained during step 108 should display bi-phasic behavior, in which small pores of the sample are only filled with brine (or de-ionized water) and large pores of the sample are only filled with hydrocarbon (pure alkane liquids such as Dodecane). If this bi-phasic behavior of different pore systems is not achieved, the sample has to treated again according to steps 100 through 108, except the $T_1(T_2)$ NMR relaxometry measurement in step 104.

Step 110 involves measurement of $T_1(T_2)$ NMR relaxometry of the same sample at $S_{wirr}$ with a low-field NMR instrument of the type described above. This is performed to achieve $T_1(T_2)$ distributions of pores in the sample saturated with hydrocarbon at $S_{wirr}$ (parameter B of Equation above). During step 112, the water and hydrocarbon fluid in the rock is removed by centrifuge, and the sample oven-dried to fully remove all fluids in the sample.

In step 114, the sample after fluid removal during step 112 is now fully saturated with the same hydrocarbon fluid used in step 106. Step 116 involves obtaining a measure of $T_1(T_2)$ NMR relaxometry of the sample with the previously described low-field NMR instrument to achieve $T_1(T_2)$ distributions of pores in the sample fully saturated with hydrocarbon, to obtain parameter α, as will be discussed.

In step 118 the connectivity of the rock sample is determined according to Equation (1), by a computer of any conventional type of suitable processing capacity, such as a personal computer, laptop computer, hand-held computer or calculator, or any other suitable processing apparatus. The determination of rock sample connectivity during step 118 is based on the measures of parameter A, the NMR relaxation time differences obtained for the brine saturated sample during step 104, parameter B, the NMR relaxation time difference obtained from the hydrocarbon saturated rock sample at $S_{wirr}$ during step 110, and parameter α, the relaxation time difference between the large pores when 100% brine saturated and when 100% hydrocarbon saturated obtained during step 116.

With the present invention, it has been found as noted above that NMR $T_1(T_2)$ relaxation times of different pore types reflect the connectivity between the different pore types. Depending on the connectivity between pores, the location of the $T_1(T_2)$ relaxation distribution varies. In other words, when the pores are well connected, the NMR relaxation time distribution gets closer together. The shorter $T_1(T_2)$ distribution gets longer and the longer one gets shorter. Thus, the connectivity between different pore types can be measure by comparing the $T_1(T_2)$ distribution of sample with no restriction on fluid transportation between pores and the $T_1(T_2)$ distribution with full restriction on fluid transportation between pores.

When hydrocarbon fluids are injected into fully brine saturated porous media with multiple pore types in completely water-wet condition, the hydrocarbon fluid cannot, due to capillary pressure, invade to the small pores which are fully saturated with brine. The $T_1(T_2)$ distributions of this sample represent those of a completely isolated pore system. With fully connected pores, the relaxation time distribution is the same for both sample conditions. Conversely, with no connectivity, the relaxation time distributions are identically separated from each other for the two sample conditions. Therefore, by comparing the $T_1(T_2)$ distribution of fully brine saturated with the distribution of the sample when hydrocarbon saturated at $S_{wirr}$, the connectivity of pores can be measured.

Figure 4A:
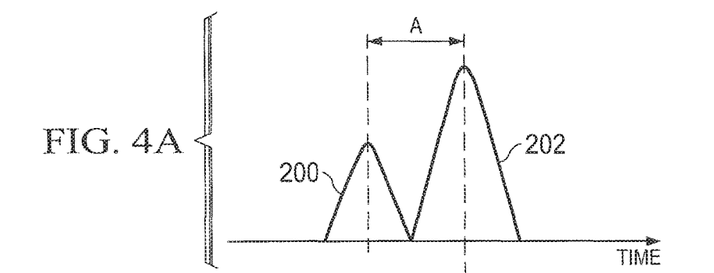
FIG. 4A is an example plot of NMR relaxation distribution time distribution between pores of a rock sample saturated with brine during the process according to FIG. 3.
Figure 4B:
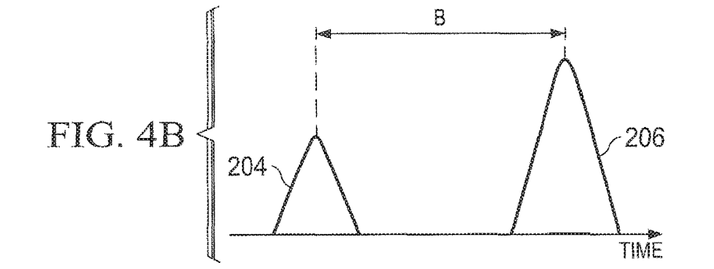
FIG. 4B is an example plot of NMR relaxation distribution time distribution between pores of a rock sample saturated with hydrocarbon at irreducible water saturation during the process according to FIG. 3.
Figure 4C:
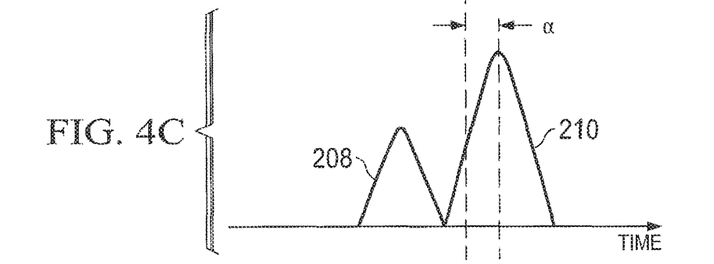
FIG. 4C is an example plot of logarithmic mean relaxation time between two pores of a rock sample saturated with hydrocarbon during the process according to FIG. 3.

The proposed definition of the connectivity is shown in FIGS. 4A, 4B, and 4C. FIG. 4A is an example plot of T1 NMR relaxation time distribution between pores of a rock sample saturated with brine during the process according to FIG. 3. As shown in FIG. 4A, a $T_1$ NMR distribution, 200 and 202, is obtained during step 104 of the process shown in FIG. 3 in the manner described above are displayed on a logarithmic time scale. The $T_1$ distribution 200 and 202 are separated from each other be an interval defined as the parameter A defining the $T_{1LM}$ between two pores saturated with brine, as described above. The same connectivity derivation, definition, and example are equally applicable for T2 NMR relaxation time distribution according to the present invention.

FIG. 4B is an example plot of NMR relaxation distribution time distribution between pores of a rock sample saturated with hydrocarbon at irreducible water saturation during the process according to FIG. 3. As shown in FIG. 4, a $T_1$ NMR distribution 204 and 206 obtained during step 110 of the process shown in FIG. 3 in the manner described above are displayed on the same logarithmic time scale as FIG. 4A. It can be seen that the $T_1$ NMR distribution 204 and 206 are moved on the scale from the distributions 200 and 202 of FIG. 4A. Further, the $T_1$ distribution from step 110 shown at 206 is moved from the $T_1$ distribution from the same step by the parameter B defining the $T_{1LM}$ between two pores saturated with hydrocarbon at $S_{wirr}$, as described above.

FIG. 4C illustrates schematically an example plot of NMR relaxation distribution time distribution between pores of a rock sample fully saturated with hydrocarbon during the process according to FIG. 3. As shown in FIG. 4C, a $T_1$ NMR distribution 208 and 210 obtained during step 116 of the process shown in FIG. 3 in the manner described above are displayed on the same logarithmic time scale as FIG. 4A. It can also be seen that the $T_1$ NMR distribution 208 and 210 are moved on the scale from the distributions 200 and 202 of FIG. 4A. It can also be seen that the $T_1$ distribution 210 from step 116 is moved from the $T_1$ distribution 202 obtained from the sample during step 104 by a parameter α representing the $T_{1LM}$ of large pores in the sample when 100% brine saturated and the same pores when 100% hydrocarbon saturated. FIG. 4C has been placed below FIG. 4A so that the parameter of representing the difference can be more clearly seen.

According to the physical rock conditions expressed in Equation (1), when pores are fully connected, then A becomes 0, which leads to the connectivity=1. In the other extreme, when pores are completely isolated A≈B, which leads to the connectivity≈0. The cause of deviation from 0 in the case of a completely isolated pore system is that B is measured from the pores saturated with different types of fluids, brine, and hydrocarbon. This difference is adjusted according to the present invention by the parameter, α, which is the difference of $T_{1LM}$ of larger pores from 100% brine saturated and 100% hydrocarbon fully saturated sample. To minimize any error caused by α, using light hydrocarbon has similar $T_1$ distribution as brine.

Figure 6:
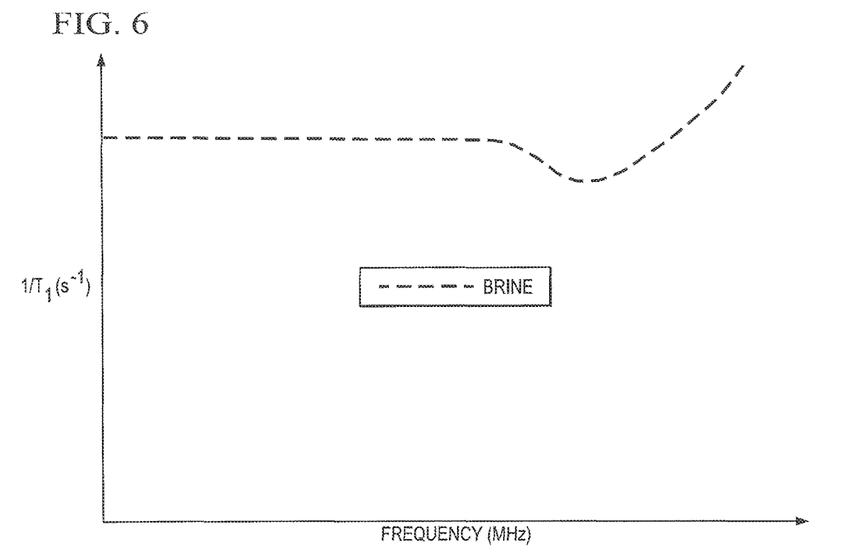
FIG. 6 is an example plot of a nuclear magnetic relaxation dispersion or NMRD profile of a rock sample saturated with brine during the process according to FIG. 3.
Figure 7:
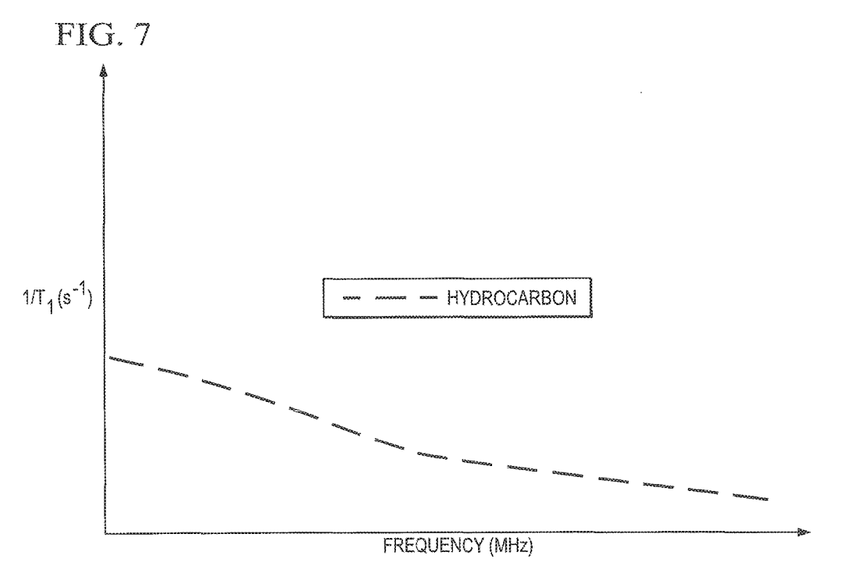
FIG. 7 is an example plot of a nuclear magnetic relaxation dispersion or NMRD profile of a rock sample saturated with hydrocarbon during the process according to FIG. 3.

Fluid isolation in multiple pore system where the parameter B can be confirmed when data for that parameter is being acquired. Due to the existence of paramagnetic ions on reservoir rocks, the NMRD's of water and hydrocarbon are different. The present invention uses this clear detectability of water and hydrocarbon in different pores systems. The measured NMRD profile acquired during step 108 can identify each pore type by accurately detecting the fluid in each pore system. This can be seen by comparison of representative example plots of an NMRD profile for brine in FIG. 6, and an NMRD profile for hydrocarbon in FIG. 7.

The $T_1$ relaxation time in the porous media can be expressed as shown in Equation (2).

$$\frac{1}{T_1(\omega_I)} = \frac{1}{T_{1,bulk}} + \frac{N_{surface}}{N}\frac{1}{T_{1,2D}(\omega_I)} + \frac{N_{param}}{N}\frac{1}{T_{1,param}(\omega_I)} \qquad (2)$$

where $T_{1,bulk}$ is the $T_1$ relaxation time of bulk fluid, $N_{surface}/N$ is the ratio between the number of liquid molecules diffusion within the thin transient layer close to the pore surface and in the bulk, $T_{1,2D(\omega_1)}$ is $T_1$ relaxation time due to 2D diffusional motion on the surface, $N_{param}/N$ is the ratio between the number of liquid molecules bonded to the paramagnetic sites at the surface and in the bulk, and $T_{1,param}$ is the $T_1$ relaxation time dominated by the interaction of proton with paramagnetic ions on the surface.

Figure 5:
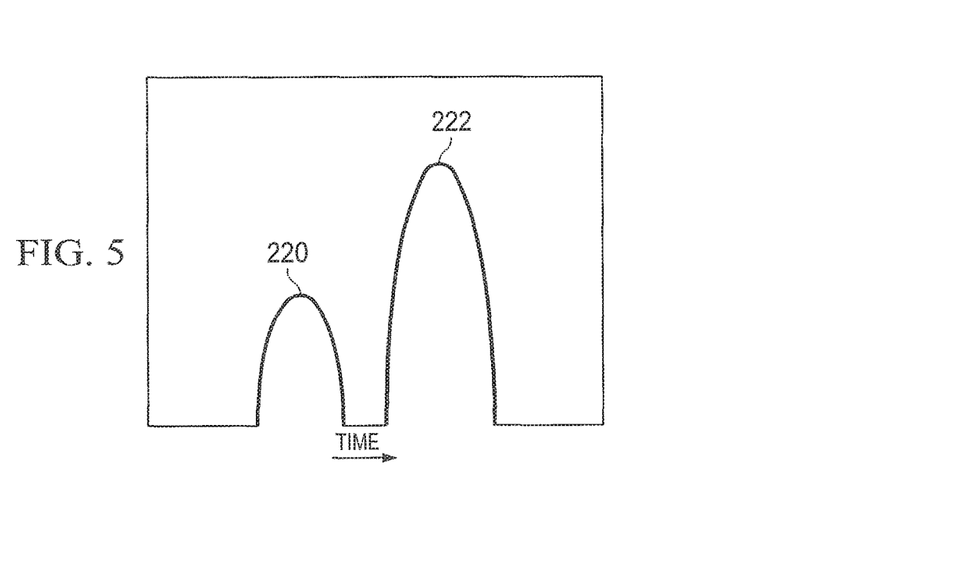
FIG. 5 is an example plot of NMR relaxation distribution time distribution between small pores and large pores of a rock sample during the process according to FIG. 3.

The $T_1$ relaxation time of brine and hydrocarbon is dominated by $T_{1,param}$ and $T_{1,2D}$, respectively (Equations 3 and 4). Further, the $T_1$ relaxation times are distinguishable on a logarithmic time plot such as FIG. 5. The $T_1$ relaxation time for brine is shown at 220 and the $T_1$ relaxation time for hydrocarbons is shown at 222. Thus, this biphasic behavior of brine and hydrocarbon in the porous media is utilized to identify the type of fluids in the specific pores in the porous media of interests.

$$\frac{1}{T_{1,aprotic}(\omega_I)} = \frac{1}{T_{1,hydrocarbon}(\omega_I)} = \frac{1}{T_{1,bulk}} + \frac{N_{surface}}{N}\frac{1}{T_{1,2D}(\omega_I)} \quad (3)$$

$$\frac{1}{T_{1,protic}(\omega_I)} = \frac{1}{T_{1,brine}(\omega_I)} = \frac{1}{T_{1,bulk}} + \frac{N_{param}}{N}\frac{1}{T_{1,param}(\omega_I)} \quad (4)$$

In the case the amount of paramagnetic ion on the surface of porous media is not enough to produce the diphasic NMRD profile form brine and hydrocarbon, it has to be treated with a certain amount of paramagnetic ions before. The result of the treatment with paramagnetic ions can be confirmed by the comparison of $T_1(T_2)$ NMR distribution before and after the treatment. Once injected paramagnetic ions coated all pores, then $T_1(T_2)$ distribution of all pore types shift toward shorter time.

The invention has been sufficiently described so that a person with average knowledge in the matter may reproduce and obtain the results mentioned in the invention herein. Nonetheless, any skilled person in the field of technique, subject of the invention herein, may carry out modifications not described in the request herein, to apply these modifications to a determined structure, or in the manufacturing process of the same, requires the claimed matter in the following claims; such structures shall be covered within the scope of the invention.

It should be noted and understood that there can be improvements and modifications made of the present invention described in detail above without departing from the spirit or scope of the invention as set forth in the accompanying claims.

What is claimed is:

1. A method of obtaining a measure of connectivity between pores in a rock sample from a subsurface hydrocarbon reservoir, comprising the steps of:
   fully saturating the rock sample with water;
   performing relaxometry of the rock sample in a nuclear magnetic resonance instrument to obtain nuclear magnetic relaxation time distributions of the pores of the rock sample fully saturated with water;
   conducting forced drainage of the rock sample to obtain irreducible water saturation of the rock sample;
   obtaining in a nuclear magnetic resonance instrument a nuclear magnetic resonance dispersion profile of the pores of the rock sample at irreducible water saturation;
   performing relaxometry of the rock sample in a nuclear magnetic resonance instrument to obtain nuclear magnetic relaxation time distributions of the pores of the rock sample at irreducible water saturation;
   fully saturating the rock sample with a hydrocarbon liquid at irreducible water saturation of the rock sample;
   performing relaxometry of the rock sample in a nuclear magnetic resonance instrument to obtain nuclear magnetic relaxation time distributions of the pores of the rock sample fully saturated with the hydrocarbon liquid; and
   processing the obtained nuclear magnetic resonance relaxation time distributions of the pores of the rock sample and the nuclear magnetic resonance dispersion profile pores of the rock sample to obtain the measure of connectivity between the pores in the rock sample from the subsurface hydrocarbon reservoir.

2. The method of claim 1, further including the step of cleaning the rock sample to obtain a water-wet rock sample prior to the step of fully saturating the rock sample with water.

3. The method of claim 1, wherein the step of obtaining a nuclear magnetic resonance dispersion profile of the rock sample comprises fast field cycling nuclear magnetic resonance relaxometry.

4. The method of claim 1, wherein the rock sample comprises a carbonate rock.

5. The method of claim 1, wherein the step of performing relaxometry to obtain nuclear magnetic resonance relaxation time distributions of the pores of the fully water saturated rock sample is performed by a low-field nuclear magnetic resonance instrument.

6. The method of claim 1, wherein the step of performing relaxometry to obtain nuclear magnetic resonance relaxation time distributions of the pores of the rock sample at irreducible water saturation is performed by a low-field nuclear magnetic resonance instrument.

7. The method of claim 1, wherein the step of performing relaxometry to obtain nuclear magnetic resonance relaxation time distributions of the pores of the fully hydrocarbon liquid saturated rock sample is performed by a low-field nuclear magnetic resonance instrument.

8. The method of claim 1, wherein the step of obtaining a nuclear magnetic resonance dispersion profile of the rock sample at irreducible water saturation is performed by a fast field cycling nuclear magnetic resonance instrument.

9. A method of obtaining a measure of connectivity between pores in a rock sample from a subsurface hydrocarbon reservoir, comprising the steps of:
   fully saturating the rock sample with water;
   performing relaxometry of the rock sample in a low-field nuclear magnetic resonance instrument to obtain nuclear magnetic resonance relaxation time distributions of the pores of the rock sample fully saturated with water;
   conducting forced drainage of the rock sample to obtain irreducible water saturation of the rock sample;
   obtaining in a fast field cycling nuclear magnetic resonance instrument a nuclear magnetic resonance dispersion profile of the pores of the rock sample at irreducible water saturation;
   performing relaxometry of the rock sample in a low-field nuclear magnetic resonance instrument to obtain nuclear magnetic resonance relaxation time distributions of the pores of the rock sample at irreducible water saturation;
   fully saturating the rock sample with a hydrocarbon liquid at irreducible water saturation of the rock sample;
   performing relaxometry of the rock sample in a low-field nuclear magnetic resonance instrument to obtain nuclear magnetic resonance relaxation time distributions of the pores of the rock sample fully saturated with the hydrocarbon liquid; and
   processing the obtained nuclear magnetic resonance relaxation time distributions of the pores of the rock sample and the nuclear magnetic resonance dispersion profile pores of the rock sample to obtain the measure of connectivity between the pores in the rock sample from the subsurface hydrocarbon reservoir.

\* \* \* \* \*